Sept. 11, 1956 W. FLEMER III Plant Pat. 1,515
HONEYLOCUST TREE
Filed Nov. 16, 1955
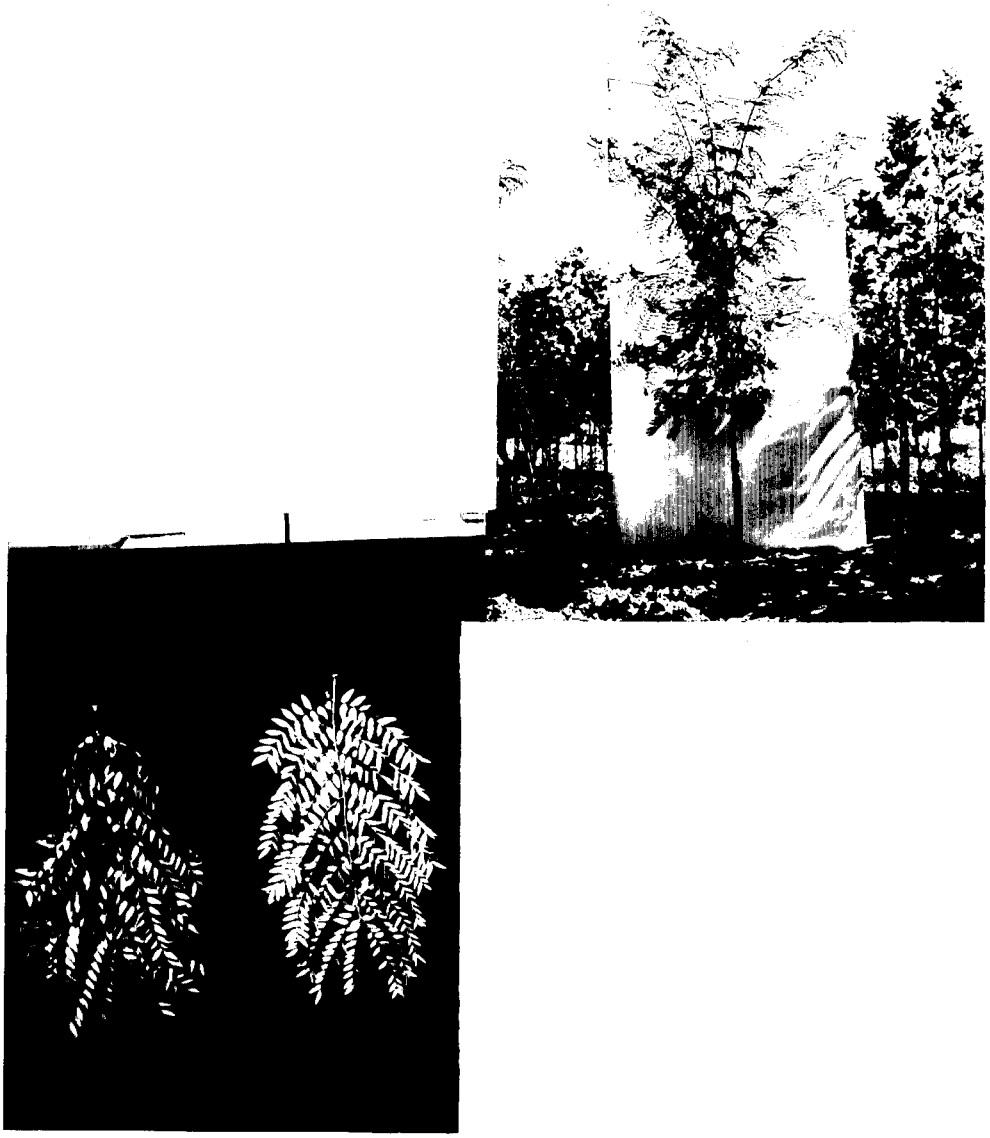
Inventor.
William Flemer, III
By: Robb & Cobb
Attorneys.

United States Patent Office

Plant Pat. 1,515

Patented Sept. 11, 1956

1,515

HONEY LOCUST TREE

William Flemer III, Princeton, N. J., assignor to Wm. Flemer's Sons, Inc., trading as Princeton Nurseries, Princeton, N. J., a corporation of New Jersey Application November 16, 1955, Serial No. 547,347

1 Claim. (Cl. 47—59)

The present invention relates to a new and distinct variety of thornless honey locust tree which was discovered by me as a newly found seedling of *Gleditsia triacanthus inermis* in transplanted blocks of seedlings of the latter variety which were being grown under my control, direction and supervision in Plainsboro Township, Plainsboro, New Jersey. At the time of my discovery, the new seedling was about 13 feet tall, and my attention was initially drawn thereto by its extremely straight and sturdy trunk, ascending branches, complete absence of any inclination to have a drooping head or a wind-blown appearance, its very symmetrical, well-balanced, even and high head, its rich dark green foliage which was extremely heavy and dense, and its relatively broad leaves which were substantially broader than those of conventional varieties.

Following my initial discovery, I promptly took steps to preserve and observe the new seedling, as well as to asexually reproduce the same by budding, as performed by me at Princeton, New Jersey. Continued observations of the original seedling and the asexual reproductions thereof have fully demonstrated that the aforementioned characteristics and distinctions are firmly established and are transmissible by asexual reproduction.

Although the parentage of my new seedling is not definitely known to me, I am convinced that it represents a new and improved variety which is distinct from all other varieties, as evidenced by the aforementioned characteristics, and by the holding of its foliage much later in the fall than conventional varieties, the retention of the rich dark green color of the foliage later in the fall than is the case with conventional varieties, and its relatively faster growth. These characteristics, and more particularly the ascending branches and high head of the tree, make the new variety ideal for street plantings, since the tree would neither interfere with nor likely be damaged by traffic.

The accompanying drawing shows a typical tree of my new variety, as well as typical specimens of the foliage thereof as the latter appears from both its upper and under surfaces on an enlarged scale, all as depicted in color as nearly true as it is reasonably possible to make the same in a color illustration of this character.

The following is a detailed description of my new variety, with color terminology in accordance with Munsell's Color Chart, except where general color terms of ordinary dictionary significance are obvious:

*Parentage:* Newly found seedling of unknown parentage.

*Propagation:* Holds its distinguishing characteristics through succeeding propagations by budding (sometimes termed "bud-grafting").

*Locality where grown and observed:* Princeton, New Jersey.

*Tree:* Large; very vigorous; upright; dense; vase-formed; symmetrical; hardy; with very symmetrical, even, well-balanced high head and having no tendency to droop, and complete absence of wind-blown appearance.

*Growth.*—Fast.

*Trunk.*—Stocky; sturdy; exceptionally straight; smooth.

*Branches.*—Medium size; very straight; ascending; smooth; glossy. Color—Brown, Plate 2.5 Y 3/2.

*Lenticels.*—Medium number; small.

*Leaves.*—Leathery; large; bipinnate; 17 or 18 pinnae per leaf and 23 or 24 leaflets per pinna; extremely heavy; dense; hold on later in fall. Average length of leaves—from 30 to 40 cm. Average width of leaves—from 28 to 38 cm. Color: upper surface—dark Nile green, Plate 10.0 GY 3/4; under surface—emerald green, Plate 10.0 GY 5/8.

*Leaflets.*—Oblong; lanceolate. Average length of individual leaflets—from 2½ to 3 cm. Average width of individual leaflets—from 7 to 9 mm.

*Rachis.*—Pubescent; markedly grooved.

*Margin.*—Remotely crenulate.

*Petiole.*—Long; medium thick.

*Glands.*—None.

*Stipules.*—Produced only on very earliest leaves in growing season; from 2 to 2½ cm. long.

*Flower buds:* Depressed; inconspicuous; small; short; plump; scarcely pubescent.

*Flowers:* Small; few; only staminate flowers observed; bloom about mid-season as compared with other varieties. Color—Pale Lemon Yellow, Plate 7.5 Y 8/6.

*Fruit:* None observed.

*Disease and insect resistance:* Foliage has proved particularly resistant to spider mite damage as compared with other varieties grown under comparable cultural conditions at Princeton, New Jersey.

I claim:

A new and distinct variety of thornless honey locust tree, substantially as herein shown and described, characterized particularly as to novelty by its extremely straight and sturdy trunk and very straight ascending branches, its very symmetrical, even, well-balanced and high head, its complete absence of thorns, its relatively fast growth, its complete absence of any wind-blown appearance in its top, its exceptionally heavy, dense, broad foliage and the rich dark green color thereof, and its habit of holding its foliage and retaining the color thereof much later in the fall as compared with other conventional varieties.

No references cited